(12) United States Patent
Ragosta et al.

(10) Patent No.: US 12,102,401 B2
(45) Date of Patent: Oct. 1, 2024

(54) STAPLER BEAM ARCHITECTURE

(71) Applicant: Intuitive Surgical Operations, Inc., Sunnyvale, CA (US)

(72) Inventors: Nicholas Ragosta, Sunnyvale, CA (US); Matthew A. Wixey, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 61 days.

(21) Appl. No.: 17/478,721

(22) Filed: Sep. 17, 2021

(65) Prior Publication Data

US 2022/0071719 A1 Mar. 10, 2022

Related U.S. Application Data

(63) Continuation of application No. 16/331,663, filed as application No. PCT/US2017/050735 on Sep. 8, 2017, now Pat. No. 11,166,773.
(Continued)

(51) Int. Cl.
*A61B 34/35* (2016.01)
*A61B 17/072* (2006.01)
(Continued)

(52) U.S. Cl.
CPC ........ *A61B 34/35* (2016.02); *A61B 17/07207* (2013.01); *A61B 2017/00309* (2013.01);
(Continued)

(58) Field of Classification Search
CPC .............. A61B 34/35; A61B 17/07207; A61B 2034/305; A61B 2017/00367;
(Continued)

(56) References Cited

U.S. PATENT DOCUMENTS 4,473,077 A * 9/1984 Noiles .................. A61B 17/115
227/19
4,606,343 A * 8/1986 Conta .................. A61B 17/115
227/178.1
(Continued)

FOREIGN PATENT DOCUMENTS

CN 103431913 A 12/2013
CN 103717147 A 4/2014
(Continued)

OTHER PUBLICATIONS

CN Office Action dated Apr. 13, 2022, in Application No. CN201780055258.3 with English Translation, 21 pages.
(Continued)

*Primary Examiner* — Lucas E. A. Palmer
(74) *Attorney, Agent, or Firm* — Farber LLC

(57) ABSTRACT

An end effector that can have an upper jaw and a lower jaw. A wrist can connect the end effector to an elongated shaft. A beam member can be arranged to translate within the upper and lower jaw. An actuation assembly can have a pushing assembly configured to transfer compressive force to the beam member and a pulling assembly configured to transfer tensile force to the beam member.

18 Claims, 16 Drawing Sheets

Related U.S. Application Data

(60) Provisional application No. 62/385,636, filed on Sep. 9, 2016.

(51) Int. Cl.
    *A61B 17/00*           (2006.01)
    *A61B 17/29*           (2006.01)
    *A61B 34/30*           (2016.01)

(52) U.S. Cl.
    CPC ............. *A61B 2017/00367* (2013.01); *A61B 2017/00477* (2013.01); *A61B 2017/00867* (2013.01); *A61B 2017/07271* (2013.01); *A61B 2017/07278* (2013.01); *A61B 2017/07285* (2013.01); *A61B 2017/2902* (2013.01); *A61B 2017/2927* (2013.01); *A61B 2034/305* (2016.02)

(58) Field of Classification Search
    CPC ........... A61B 2017/00477; A61B 2017/00867; A61B 2017/07278
    See application file for complete search history.

(56) References Cited

U.S. PATENT DOCUMENTS

| | | | | |
|---|---|---|---|---|
| 4,646,745 | A * | 3/1987 | Noiles | A61B 17/115 227/19 |
| 5,139,513 | A * | 8/1992 | Segato | A61B 17/115 227/180.1 |
| 5,246,156 | A * | 9/1993 | Rothfuss | A61B 17/0684 227/176.1 |
| 5,271,543 | A * | 12/1993 | Grant | A61B 17/115 227/19 |
| 5,433,721 | A * | 7/1995 | Hooven | A61B 17/068 606/139 |
| 5,465,894 | A * | 11/1995 | Clark | A61B 17/072 227/19 |
| 5,797,538 | A * | 8/1998 | Heaton | A61B 17/07207 227/176.1 |
| 6,171,316 | B1 * | 1/2001 | Kovac | A61B 17/062 606/205 |
| 6,179,809 | B1 * | 1/2001 | Khairkhahan | A61M 25/0147 604/95.04 |
| 6,443,973 | B1 * | 9/2002 | Whitman | A61B 17/1114 227/176.1 |
| 7,922,742 | B2 * | 4/2011 | Hillstead | A61B 17/07207 606/174 |
| 8,992,422 | B2 | 3/2015 | Spivey et al. | |
| 9,028,494 | B2 | 5/2015 | Shelton, IV et al. | |
| 11,166,773 | B2 | 11/2021 | Ragosta et al. | |
| 2007/0250113 | A1 * | 10/2007 | Hegeman | A61B 1/0055 606/207 |
| 2009/0312773 | A1 * | 12/2009 | Cabrera | A61B 17/0469 606/144 |
| 2010/0023024 | A1 * | 1/2010 | Zeiner | A61B 17/0469 606/144 |
| 2010/0023025 | A1 * | 1/2010 | Zeiner | A61B 90/94 606/144 |
| 2010/0023026 | A1 * | 1/2010 | Zeiner | A61B 17/0401 227/176.1 |
| 2010/0082046 | A1 * | 4/2010 | Harris | A61F 5/0079 606/139 |
| 2010/0174269 | A1 * | 7/2010 | Tompkins | A61B 17/12022 604/507 |
| 2010/0331857 | A1 * | 12/2010 | Doyle | A61B 34/30 901/29 |
| 2011/0006099 | A1 * | 1/2011 | Hall | A61B 17/07207 227/175.1 |
| 2011/0082471 | A1 * | 4/2011 | Holcomb | A61B 17/0401 606/139 |
| 2011/0082472 | A1 * | 4/2011 | Harris | A61B 17/0469 606/139 |
| 2011/0152879 | A1 * | 6/2011 | Williams | A61B 34/71 606/130 |
| 2011/0295242 | A1 * | 12/2011 | Spivey | A61B 17/07207 606/1 |
| 2012/0298719 | A1 * | 11/2012 | Shelton, IV | A61B 17/105 227/176.1 |
| 2013/0221059 | A1 | 8/2013 | Racenet et al. | |
| 2014/0001231 | A1 * | 1/2014 | Shelton, IV | A61B 34/71 227/175.3 |
| 2014/0005653 | A1 * | 1/2014 | Shelton, IV | A61B 18/14 606/205 |
| 2014/0005661 | A1 * | 1/2014 | Shelton, IV | A61B 34/37 606/41 |
| 2014/0214049 | A1 * | 7/2014 | Jeong | A61B 17/00234 606/130 |
| 2014/0257331 | A1 * | 9/2014 | Kim | A61B 34/30 606/130 |
| 2014/0276736 | A1 * | 9/2014 | Worrell | A61B 18/1445 606/33 |
| 2015/0173755 | A1 * | 6/2015 | Baxter, III | A61B 17/072 227/180.1 |
| 2015/0173756 | A1 * | 6/2015 | Baxter, III | A61B 17/0644 227/177.1 |
| 2015/0297199 | A1 | 10/2015 | Nicholas et al. | |
| 2015/0327868 | A1 * | 11/2015 | Islak | A61B 17/12109 606/200 |
| 2016/0228202 | A1 * | 8/2016 | Prindiville | A61B 34/30 |
| 2016/0296231 | A1 * | 10/2016 | Wang | A61B 17/068 |
| 2019/0239877 | A1 * | 8/2019 | Ragosta | A61B 34/71 |
| 2019/0239967 | A1 * | 8/2019 | Ragosta | A61B 34/35 |

FOREIGN PATENT DOCUMENTS

| | | |
|---|---|---|
| CN | 104490429 A | 4/2015 |
| CN | 104602636 A | 5/2015 |
| CN | 105559850 A | 5/2016 |
| CN | 105796138 A | 7/2016 |
| CN | 104739469 B | 2/2017 |
| EP | 0063217 A1 | 10/1982 |
| EP | 3034014 A2 | 6/2016 |
| EP | 3332717 A1 | 6/2018 |
| JP | H0833716 A | 2/1996 |
| JP | H11239619 A | 9/1999 |
| JP | 2005193061 A | 7/2005 |
| JP | 2006501954 A | 1/2006 |
| JP | 2007252921 A | 10/2007 |
| JP | 2015525612 A | 9/2015 |
| JP | 2015205170 A | 11/2015 |
| JP | 2017538532 A | 12/2017 |
| WO | WO-03001986 A2 | 1/2003 |
| WO | WO-2004032762 A1 | 4/2004 |
| WO | WO-2004112618 A2 | 12/2004 |
| WO | WO-2014004248 A1 | 1/2014 |
| WO | WO-2015057990 A1 * | 4/2015 ....... A61B 17/00234 |
| WO | WO-2015096530 A1 | 7/2015 |
| WO | WO-2015127250 A1 | 8/2015 |
| WO | WO-2016100068 A1 | 6/2016 |
| WO | WO-2018049198 A1 | 3/2018 |

OTHER PUBLICATIONS

Extended European Search Report for Application No. EP17849638.6, mailed on Jul. 28, 2020, 14 pages.
International Search Report and Written Opinion for Application No. PCT/US2017/050735, mailed on Dec. 15, 2017, 15 pages.
Partial European Search Report for Application No. EP17849638.6, mailed on Apr. 29, 2020, 15 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

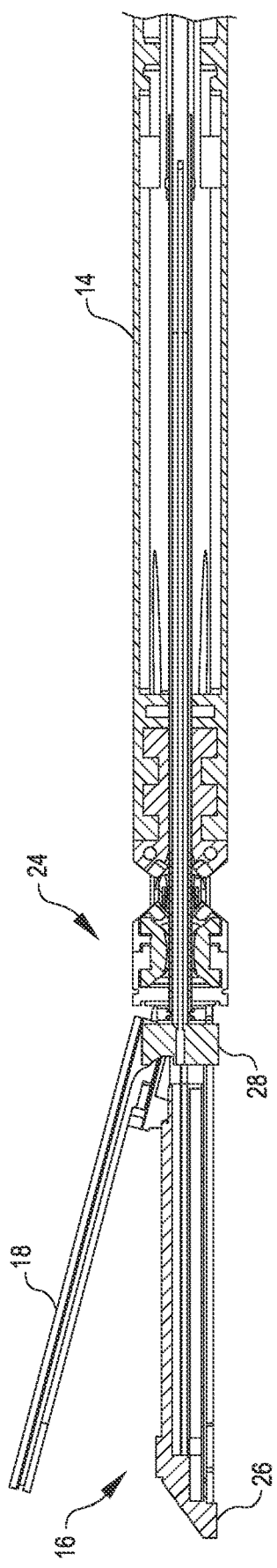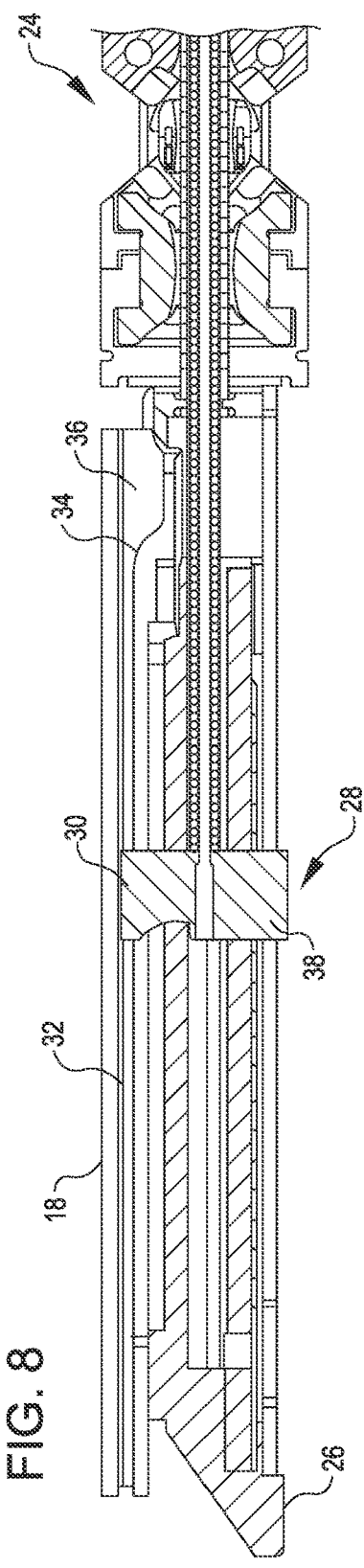

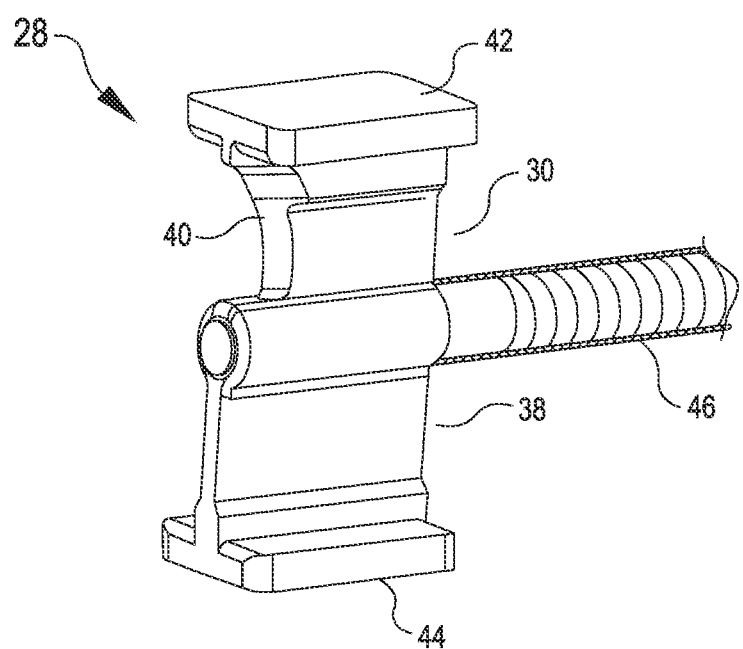

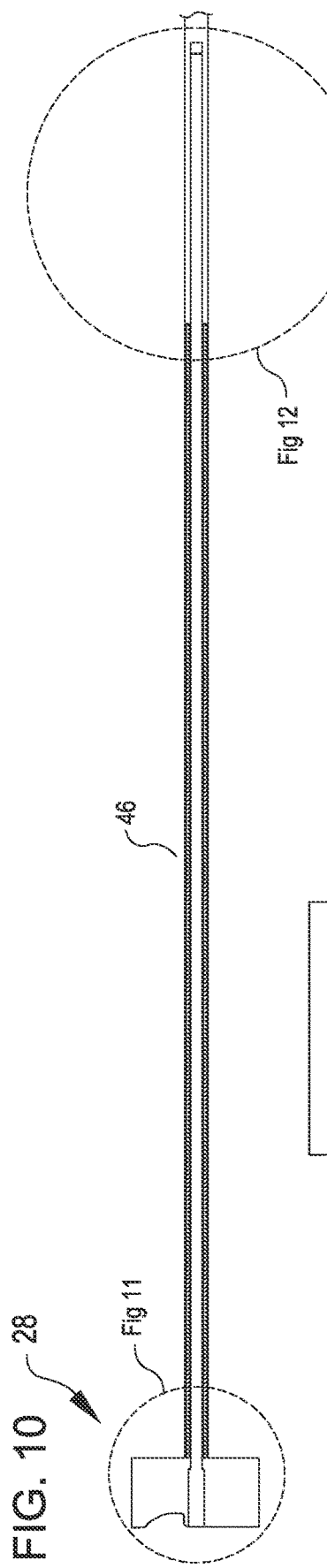
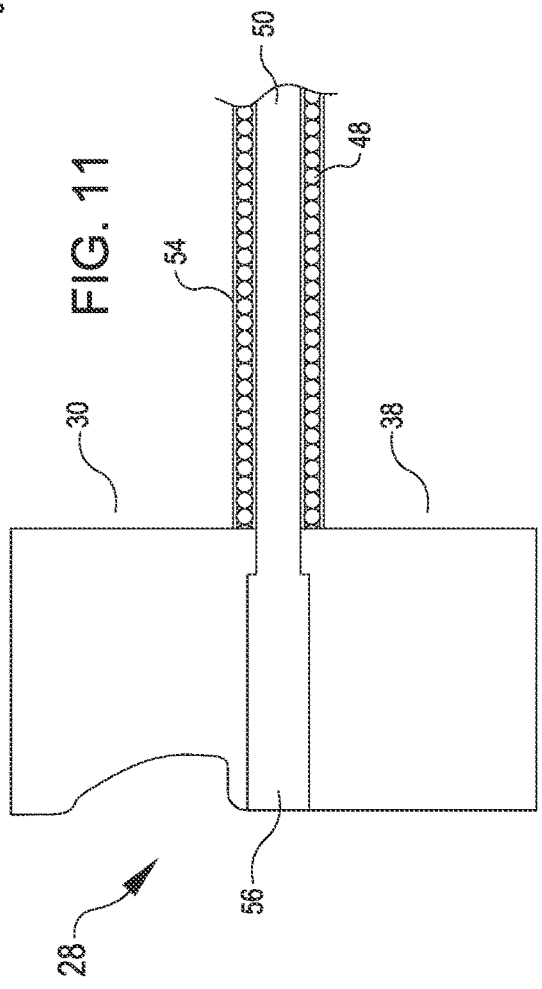
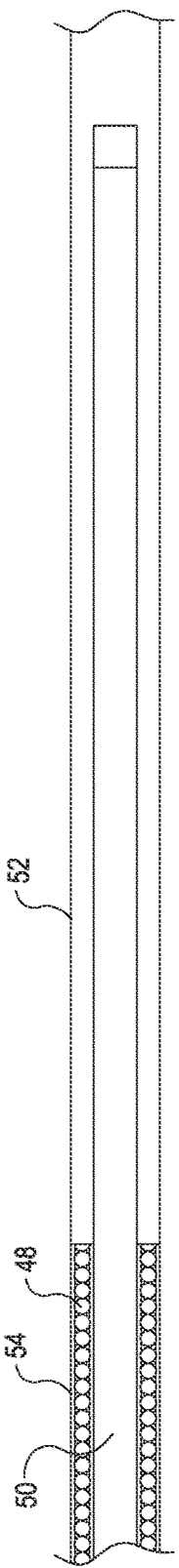
FIG. 10
FIG. 11
FIG. 12

48h

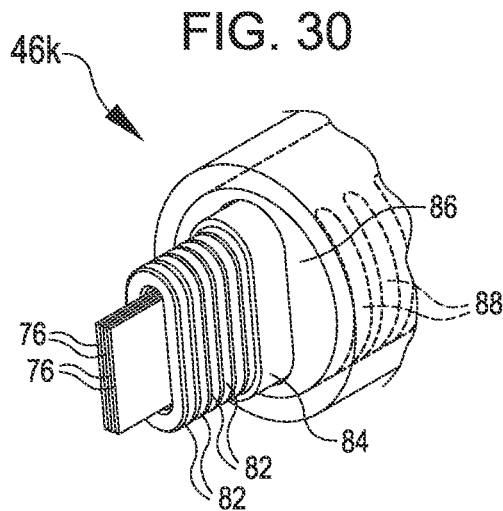
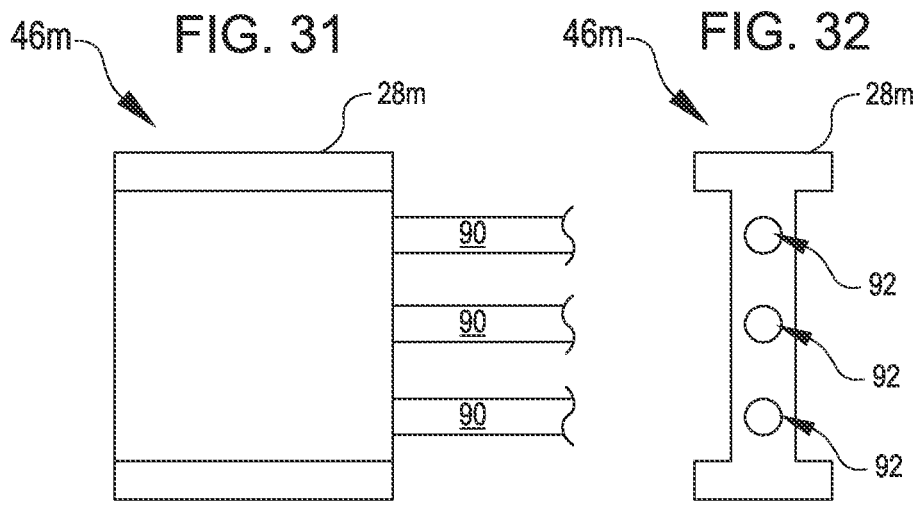
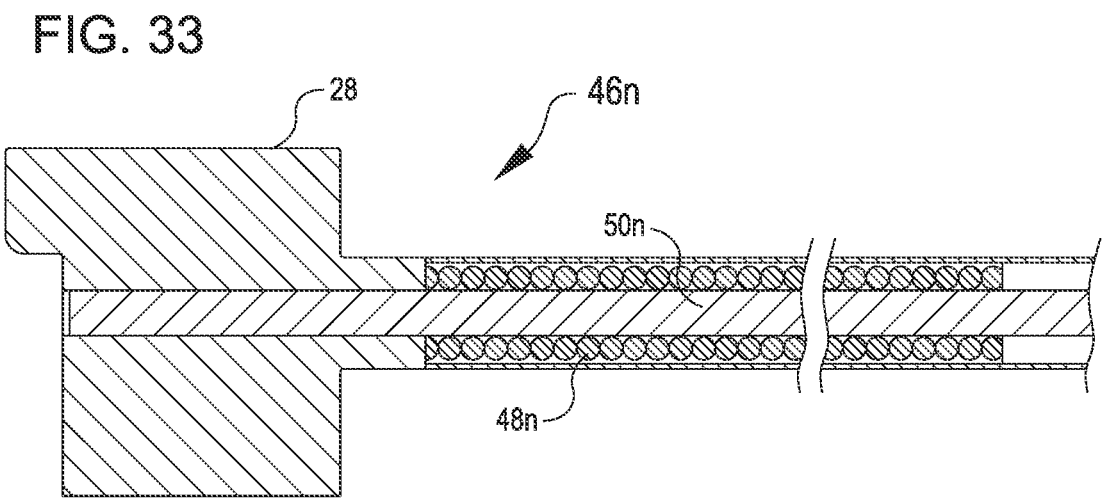

STAPLER BEAM ARCHITECTURE

CROSS REFERENCE TO RELATED APPLICATION DATA

The present application is a Continuation of U.S. patent application Ser. No. 16/331,663 filed Mar. 8, 2019 (now U.S. Pat. No. 11,166,773); which is a U.S. National Stage 371 application of PCT/US2017/050735 filed Sep. 8, 2017; which claims the benefit of U.S. Provisional Application No. 62/385,636 filed Sep. 9, 2016; the full disclosures are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and/or surgery inside the abdominal cavity. Reloadable stapling devices can be used in conjunction with laparoscopic surgeries. Telesurgically controlled stapling devices can include servo controlled wrist joints that yaw and pitch at relatively large angles (e.g., up to and over 90 degrees). The articulation of such wrist joints can place a large amount of strain on actuation components that extend through the wrist.

BRIEF SUMMARY

Embodiments disclosed herein relate to surgical devices having wrists that can yaw and pitch at relatively large angles. Such wrists can have a yaw axis spatially separated from a pitch axis, with the yaw and pitch axes being perpendicular to one another as well as to a longitudinal axis that defines the extension of an arm or shaft of a telesurgically controlled device. In some cases, the yaw and pitch angles can be up to 45, 60, or 90 degrees.

In many embodiments, a flexible actuation assembly that extends through a wrist that can yaw and/or pitch at relatively large angles includes a pulling assembly and a pushing assembly. The flexible actuation assembly can be used to open and close jaws of a surgical device and/or to actuate other implements such as cutting and/or stapling devices. In many embodiments, the pushing element can transmit compressive force even while having a substantial amount of curvature induced via high yaw and/or pitch angles of the wrist. In many embodiments, the pushing assembly does not transmit significant amount of tensile force and the pulling element is used to transmit tensile force for proximal movement and actuation of the surgical device. In a similar manner, the pulling component may not transmit significant amount of compressive force. In many embodiments, the combination of the pushing assembly and the pulling assembly into the flexible actuation assembly enables use of the flexible actuation assembly for both compressive and tensile force application (i.e., pushing and pulling) to actuate components of an end effector of a surgical device.

The pushing assembly and the pulling component can be integrated along a shared axis with the pushing component being concentrically arranged about the pulling component. In some embodiments, the pushing component includes a coiled spring and the pulling component includes a braided cable. Alternatively the pulling component can be concentrically arranged about the pushing component.

To enable a high degree of wrist flexibility, the wrist assembly can be constructed from outer links that define yaw and pitch geometry for the wrist assembly. The outer links can house a flexible portion of the actuation mechanism. However, compression of the actuation mechanism within a wrist can cause buckling and decrease efficiency of force transmission. To help mitigate such issues, inner links can be provided that connect the outer links to one another. The inner links can define a passage that constrains and limits lateral movement of the actuation mechanism, and thus mitigate buckling.

Thus, in one aspect, an apparatus is described that includes an end effector, a beam member, a pulling assembly, and a pushing assembly. The end effector includes an upper jaw and a lower jaw. A wrist connects the end effector to an elongated shaft. The beam member is arranged to translate within the upper jaw and the lower jaw. The beam member has a first portion for moveably coupling to the upper jaw and a second portion for moveably coupling to the lower jaw. The pulling assembly is connected to the beam member. The pulling assembly is flexibly housed within the wrist and applies tensile force to the beam member. The pushing assembly is connected to the beam member. The pushing assembly is flexibly housed within the wrist and applies compressive force to the beam member. In many embodiments, the wrist is configured to pitch and yaw with the pulling assembly and the pushing assembly housed therein.

The pulling assembly of the apparatus can have any suitable configuration. For example, the pulling assembly can include an elongated cable. The pulling assembly can include a braided sheath. The pulling assembly can include a plurality of sheet metal bands. The bending stiffness of the pulling assembly can be the same for actuation of the wrist that pitches the end effector relative to the elongated shaft and actuation of the wrist that yaws the end effector relative to the elongated shaft.

The pushing assembly of the apparatus can have any suitable configuration. For example, the pushing assembly can include an inner lumen that surrounds the pulling assembly. The pushing assembly can include a close-coiled spring. The close-coiled spring can have a cylindrical outer surface. The close-coiled spring can have interfacing convex and concave surfaces. The close-coiled spring can include a spiral cut tube. The pushing assembly can include a tube having a pattern of recesses that reduce bending stiffness of the tube while maintaining adequate axial stiffness to transmit compressive force to the beam member. The pushing assembly can include a plurality of pushing elements that separate under tension. The pushing assembly can include a plurality of spherical members. The pulling assembly can define an inner lumen that houses the plurality of spherical members. The spherical members can be linked by a flexible rod. The pushing assembly can include a plurality of separate elements having interfacing surfaces that limit transverse relative sliding between the elements to one direction. The pushing assembly can include a plurality of separate elements having interfacing surfaces that inhibit relative twisting between the elements. The pushing assembly can include a stack of flat washers. The pushing assembly can include a stack of torus disks. The pushing assembly can include a stack of rectangular washers defining a lumen through which the plurality of sheet metal bands extends. The bending stiffness of the pushing assembly can be the same for actuation of the wrist that pitches the end effector relative to the elongated shaft and actuation of the wrist that yaws the end effector relative to the elongated shaft.

In another aspect, a surgical tool is described that includes an end effector, a beam member, and an actuation assembly. The end effector includes an upper jaw and a lower jaw. A wrist connects the end effector to an elongated shaft. The beam member is arranged to translate within the upper jaw and the lower jaw. The beam member has a first portion for moveably coupling to the upper jaw and a second portion for moveably coupling to the lower jaw. The actuation assembly includes a pushing assembly that transfers compressive force to the beam member and a pulling assembly that transfers tensile force to the beam member. In many embodiments, the wrist is configured to pitch and yaw with the actuation assembly housed therein.

The actuation assembly of the surgical tool can have any suitable configuration. For example, the pulling assembly can include an elongated cable. The pulling assembly can include a braided sheath. The pulling assembly can include a plurality of sheet metal bands. The bending stiffness of the pulling assembly can be the same for actuation of the wrist that pitches the end effector relative to the elongated shaft and actuation of the wrist that yaws the end effector relative to the elongated shaft. The pushing assembly can include an inner lumen that surrounds the pulling assembly. The pushing assembly can include a close-coiled spring. The close-coiled spring can have a cylindrical outer surface. The close-coiled spring can have interfacing convex and concave surfaces. The close-coiled spring can include a spiral cut tube. The pushing assembly can include a tube having a pattern of recesses that reduce bending stiffness of the tube while maintaining adequate axial stiffness to transmit compressive force to the beam member. The pushing assembly can include a plurality of pushing elements that separate under tension. The pushing assembly can include a plurality of spherical members. The pulling assembly can define an inner lumen that houses the plurality of spherical members. The spherical members can be linked by a flexible rod. The pushing assembly can include a plurality of separate elements having interfacing surfaces that limit transverse relative sliding between the elements to one direction. The pushing assembly can include a plurality of separate elements having interfacing surfaces that inhibit relative twisting between the elements. The pushing assembly can include a stack of flat washers. The pushing assembly can include a stack of torus disks. The pushing assembly can include a stack of rectangular washers defining a lumen through which the plurality of sheet metal bands extends. The bending stiffness of the pushing assembly can be the same for actuation of the wrist that pitches the end effector relative to the elongated shaft and actuation of the wrist that yaws the end effector relative to the elongated shaft. A one-dimensional array of flexible rods can be used as both the pulling assembly and the pushing assembly. A nickel-titanium rod can be used as both the pulling assembly and the pushing assembly.

BRIEF DESCRIPTION OF THE DRAWINGS

FIGS. 7 and 8 show cross-sectional views of the surgical tool of FIGS. 1-6.

FIG. 9 shows an embodiment of an actuation assembly of the surgical tool of FIGS. 1-6, in accordance with some embodiments.

FIG. 10 shows a cross-sectional view of the actuation assembly of FIG. 9.

FIG. 11 shows a cross-sectional view of a distal portion of the actuation assembly of FIG. 9.

FIG. 12 shows a cross-sectional view of a proximal portion of the actuation assembly of FIG. 9.

FIG. 30 shows another embodiment of an actuation assembly of the surgical tool of FIGS. 1-6.

FIGS. 31 and 32 show views of another embodiment of an actuation assembly of the surgical tool of FIGS. 1-6.

FIG. 33 shows another embodiment of an actuation assembly of the surgical tool of FIGS. 1-6.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Figure 1:
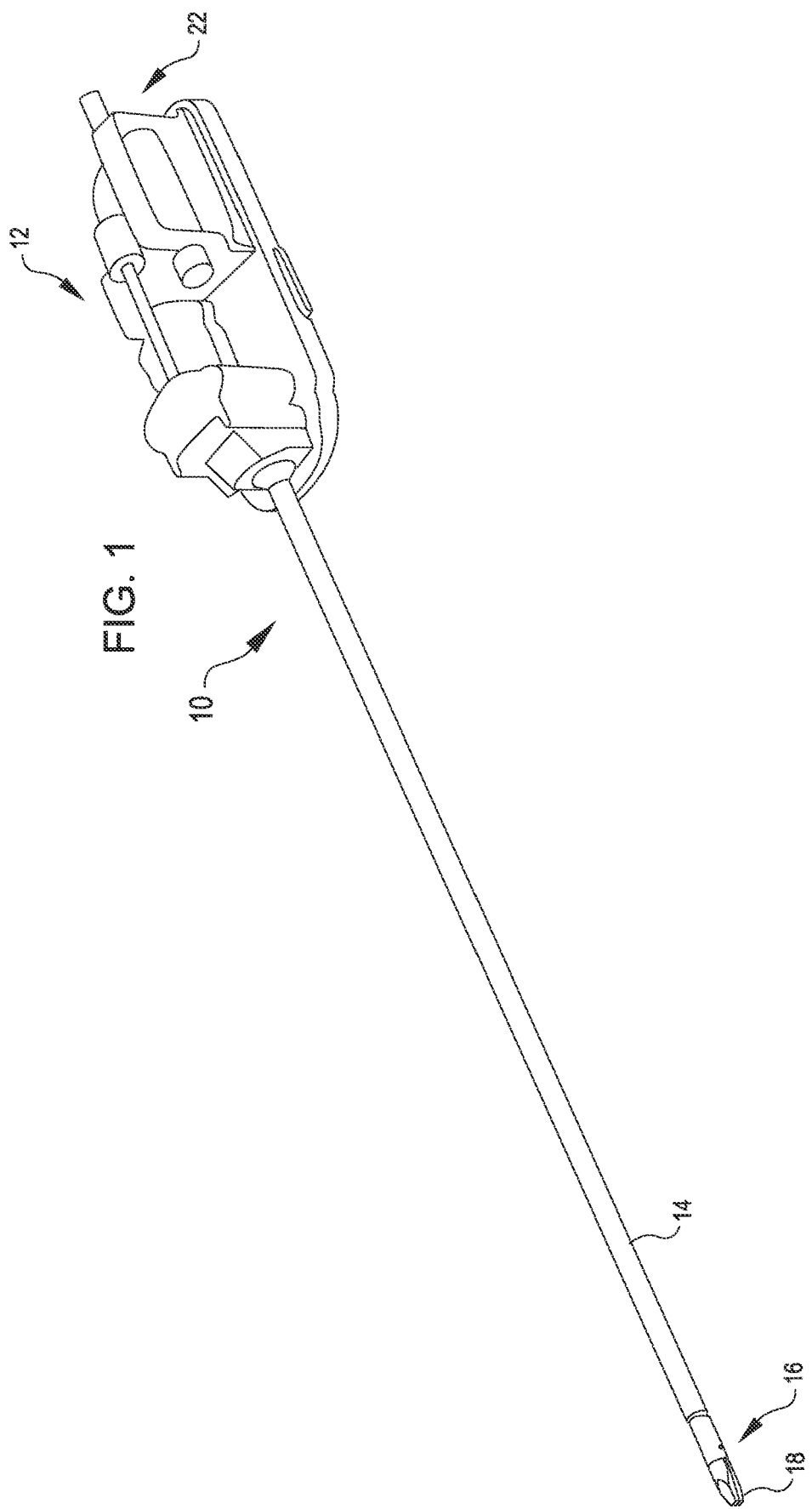
FIGS. 1-6 show views of a surgical tool, in accordance with some embodiments.
Figure 2:
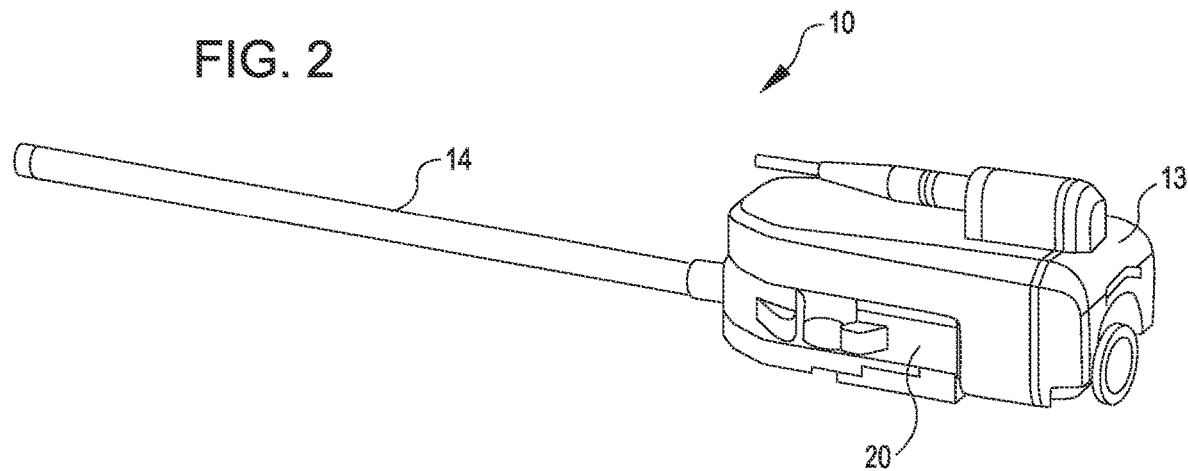
Figure 3:
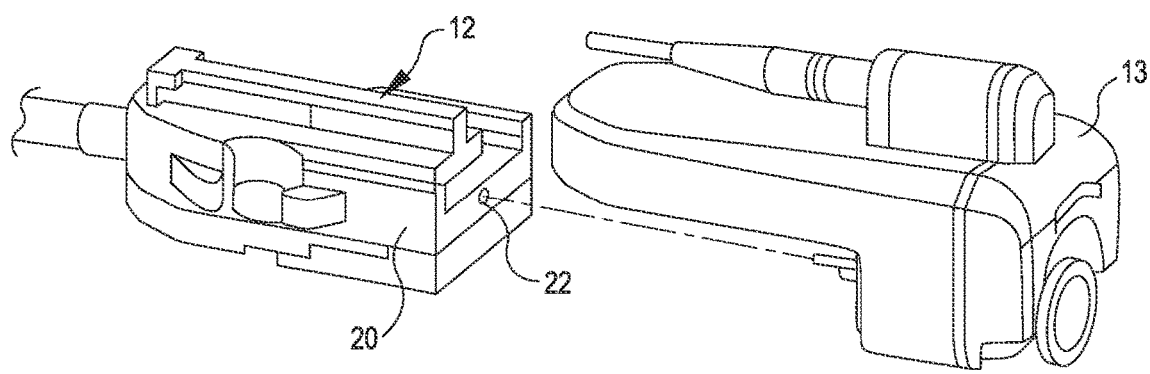

FIGS. 1-3 show a surgical tool 10 that includes a proximal chassis 12, an instrument shaft 14, and a distal end effector 16 having an upper jaw 18 that can be articulated to grip a patient tissue. The proximal chassis 12 includes input couplers 22 that may interface with and be driven by corresponding output couplers of a telesurgical surgery system, such as the system disclosed within Pub. No. US 2014/0183244 A1, which is incorporated by reference herein. The input couplers 22 are drivingly coupled with one or more input members that are disposed within the instrument shaft 14. The input members are drivingly coupled with the end effector 16. As shown at FIGS. 2 and 3, input couplers 22 of the proximal chassis 12 can be adapted to mate with various types of motor packs 13, such as stapler specific motor packs disclosed at U.S. Pat. No. 8,912,746, or the universal motor packs disclosed at U.S. Pat. No. 8,529,582, which are incorporated by reference herein.

Figure 4:
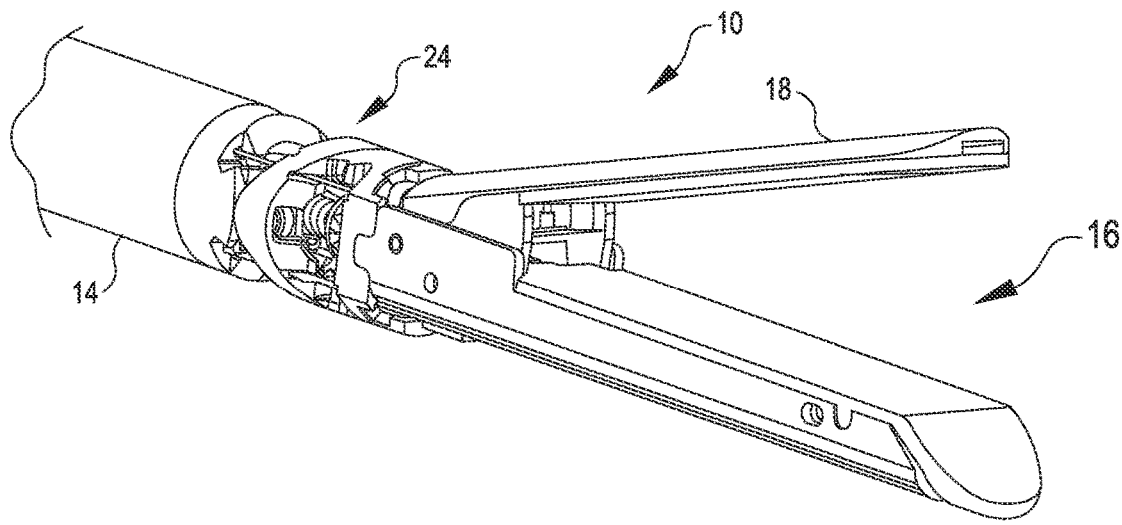
Figure 5:
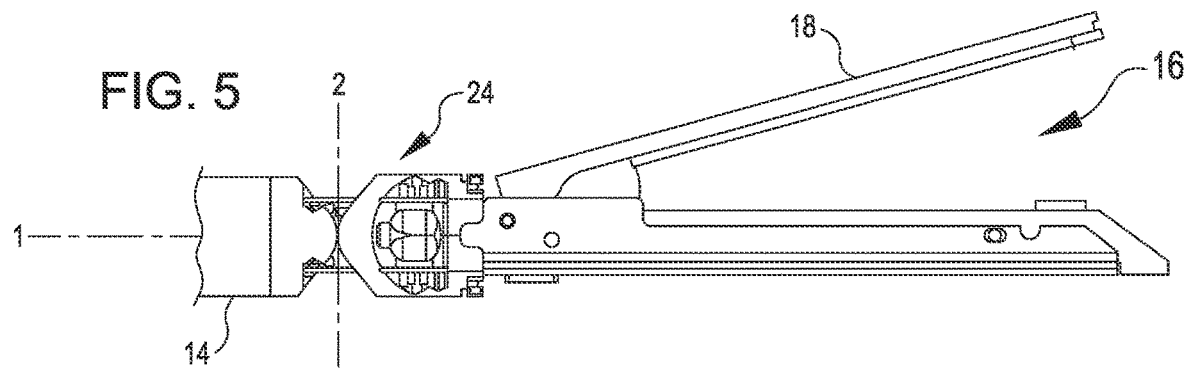
Figure 6:
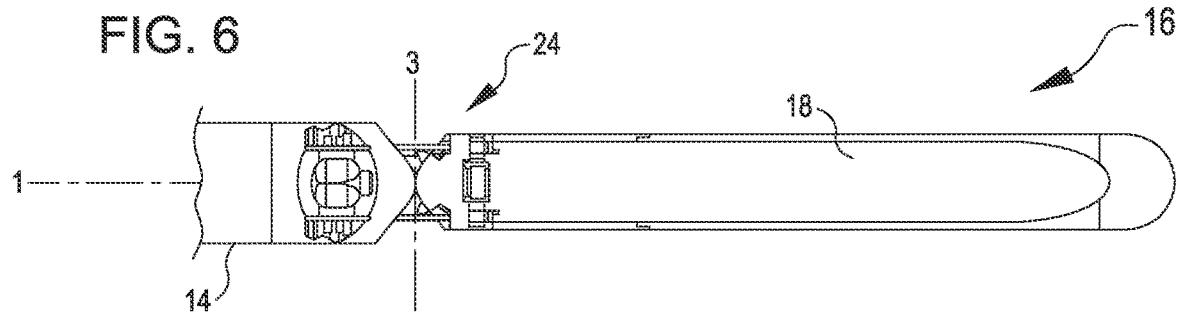

FIGS. 4-6 show perspective, side, and top views of a distal end of the surgical tool 10 including the end effector 16. End effector 16 is moveably connected to the instrument shaft 14 by a wrist assembly 24. The wrist assembly 24 has at least two degree of freedom and provides for attachment of the end effector 16 to the elongated instrument shaft 14 for articulation of the end effector 16 about two orthogonal axes relative to the instrument shaft 14. The wrist assembly 24 is configured to yaw the end effector 16 relative to the instrument shaft 14 about an axis 2, which is perpendicular to axis 1 that the instrument shaft 14 extends along. The wrist assembly 24 is also configured to pitch the end effector 16 relative to the instrument shaft 14 about an axis 3, which is perpendicular to axis 1 and axis 2. As shown, the yaw axis 2 is proximal (farther from the end effector 16) to the pitch axis 3, however this is not a requirement and in some embodiments the yaw axis 2 is distal to the pitch axis 3.

FIGS. 7 and 8 are a cross-sectional views showing details of end effector 16 that include the upper jaw 18 and a lower jaw 26. The lower jaw 26 can be configured to accommodate and support a removable or non-removable stapling cartridge. The upper jaw 18 is pivotally coupled with the lower jaw 26 to articulate relative to the lower jaw 26 to clamp tissue. A beam member 28 is driven from a proximal state shown at FIG. 7 to a distal state shown at FIG. 8 to actuate the upper jaw 18. Movement of the beam member 28 can serve to forcibly secure the upper jaw 18 over tissue with respect to the lower jaw 26. Optionally, the beam member 28 can also allow for cutting tissue and deploying staples from the cartridge into the cut tissue.

The beam member 28 includes an upper beam portion 30 that is configured to slide within a rail feature 32 of the upper jaw 18. The rail feature 32 includes a ramp 34 for the upper beam portion 30 to engage from a proximal most garage area 36. The open position shown at FIG. 7 can be maintained by a resilient device, such as a spring, or opened and closed by a secondary mechanism (not shown). Partial closure of the upper jaw 18 can be affected by distal movement of the upper beam portion 30 onto the ramp 34. Complete closure of the upper jaw 18 is achieved when the upper beam portion 30 is moved distally past the ramp 34 and onto the rail feature 32. Proximal movement of the upper beam portion 30 off of the ramp 34 removes the closure force applied to the upper jaw 18 by the beam member 28. A resilient device or secondary mechanism can then cause a closed or partially closed upper jaw 18 to open. Thus, back and forth movement of the upper beam portion 30 along the ramp 34 can toggle the end effector 16 open and closed.

The beam member 28 also includes a lower beam portion 38 that configured to slide within a rail feature of the lower jaw 18. The lower beam portion 38 can actuate a sled (such as disclosed in Pub. No. US 2014/0183244 A1) configured for ejecting staples out the lower jaw 26 during distal movement of the beam member 28. Alternatively, the lower beam portion 38 can be integrated with such a sled.

FIG. 9 shows a view of the beam member 28. Here, the upper beam portion 30 includes an integrated cutting member 40 that is configured to cut tissue. However, in other embodiments a tissue cutting device can be separate from the beam member 28 or implemented into the beam member 28 in a different manner. The upper beam portion 30 includes an upper flange 42, which transversely extends from the integrated cutting member 40. The upper flange 42 is configured to directly interface with the rail feature 32 and the ramp 34. In a similar manner a lower flange 44 is provided to slide with a rail feature of the lower jaw 26. An elongated actuation assembly 46 is attached to the beam member 28 for providing distal and proximal movement to the beam member 28.

FIGS. 10-12 show cross-sectional views of the beam member 28 and the actuation assembly 46. The actuation assembly 46 includes a pushing assembly 48 and a pulling assembly 50. In the embodiment shown, the pushing assembly 48 is configured as a close-coiled spring and is adapted to transmit compressive force from a drive rod 52 to the beam member 28. The pushing assembly 48 can be externally constrained by a sheath 54, which can be constructed from any suitable material such as, for example, a lubricous polymer material such as PTFE. The coiled design of the pushing assembly 48 allows compressive force to be translated effectively to the beam member 28 to push the beam member 28 in the distal direction. The pushing assembly 48 can be constructed in any suitable manner. For example, in some embodiments the pushing assembly 48 is constructed from a coiled wire. In some embodiments, the pushing member 48 is spirally cut from a tube. In some cases, the compressive elements (e.g., coils) of the pushing assembly will separate under tension, and thus in such cases the pushing assembly may be employed primarily to transfer compressive force.

The pulling assembly 50 can be constructed from any suitable element or elements capable of reacting tensile load (e.g., a braided cable or a flexible rod). In the embodiment shown, the pulling assembly 50 is retained within the beam member 28 by a crimp portion 56. In some cases, the pulling assembly 50 may be relatively ineffective to transfer compressive force from the drive rod 52 to the beam member 28 as it may have the tendency to collapse or buckle on itself, and thus in such cases the pulling assembly 50 may be employed primarily to transfer tensile force. The pulling assembly 50 is adapted to transmit tension force applied by the drive rod 52 to the beam member 28. The drive rod 52 is located within the instrument shaft 14 and is drivingly coupled to one or more of the input couplers 22 shown at FIG. 1. The pulling assembly 50 allows tensile force to be transmitted effectively from the drive rod 52 to the beam member 28, to pull the beam member 28 in the proximal direction. The pushing assembly 48 and pulling assembly 50 operate in a complementary manner to provide distal and proximal motion to the beam member 28 by transmitting tensile force via the pulling assembly 50 and compressive force via the pushing assembly 48. Transmitting tensile force via the pulling assembly 50 and compressive force via the pushing assembly 48 enables a very flexible and compact design for the actuation assembly 46, characteristics that enable the actuation assembly 46 to translate within the wrist 24, which can be disposed at relatively large yaw and pitch angles during operation.

Figure 13:
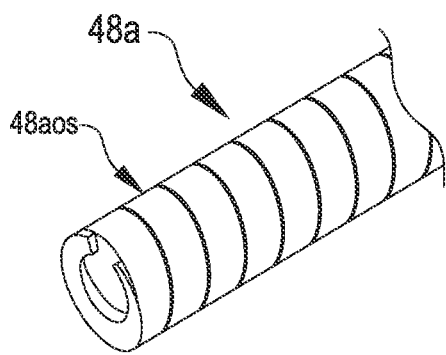
FIGS. 13 and 14 show an embodiment of a pushing assembly of an actuation assembly of the surgical tool of FIGS. 1-6.
Figure 14:
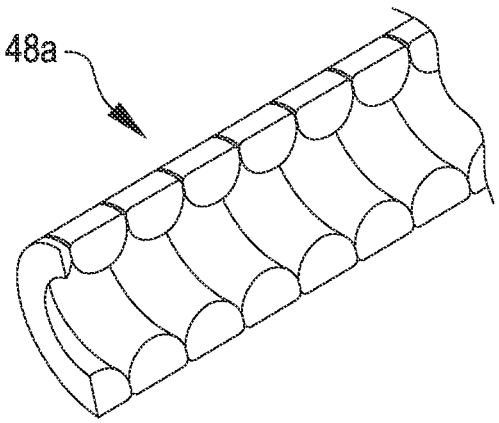

The pushing assembly 48 can have a cylindrical outer diameter to provide a substantially continuous outer profile and larger/stiffer wire section for given fixed inner and outer diameters. For example, FIGS. 13 and 14 show a pushing assembly 48a that has a cylindrical outer surface 48aos. Any suitable approach can be used to fabricate the pushing assembly 48a, such as grinding a coil spring to form the cylindrical outer surface 48aos.

Figure 15:
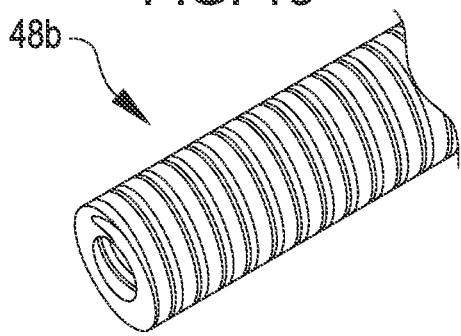
FIGS. 15 and 16 show another embodiment of a pushing assembly of an actuation assembly of the surgical tool of FIGS. 1-6.
Figure 16:
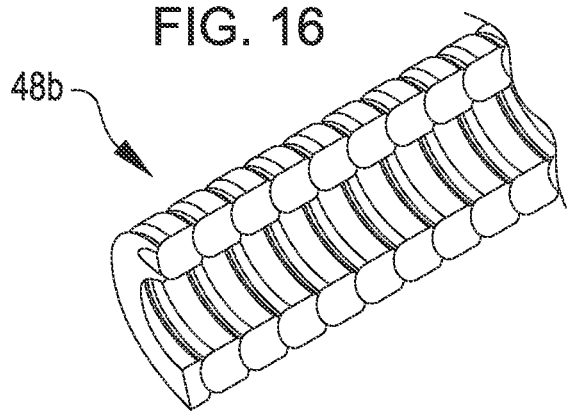

The pushing assembly 48 can include a close-coil spring having interfacing convex/concave surfaces. For example, FIGS. 15 and 16 show a pushing assembly 48b that has interfacing convex/concave surfaces that nest together with adjacent sections of the coil to increase distribution contact stresses and improve column stability relative to a round wire coil spring.

Figure 17:
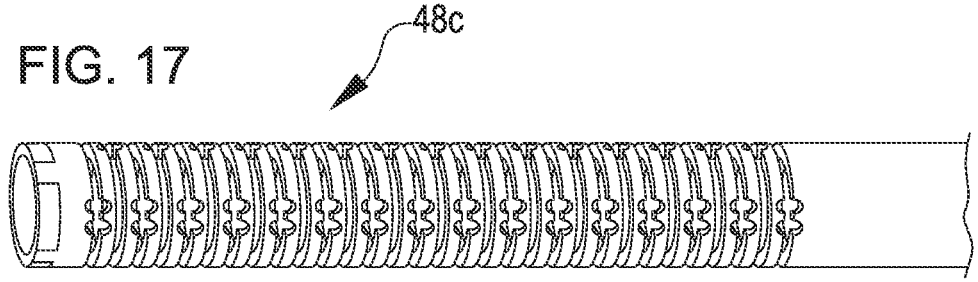
FIG. 17 shows an embodiment of a pushing assembly of an actuation assembly of the surgical tool of FIGS. 1-6.
Figure 18:
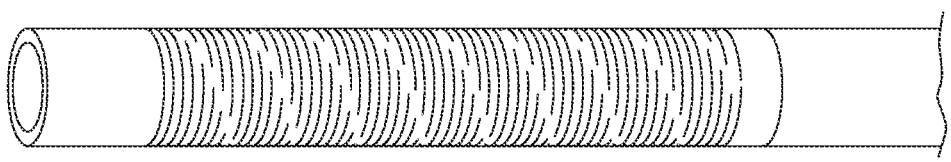
FIG. 18 shows another embodiment of a pushing assembly of an actuation assembly of the surgical tool of FIGS. 1-6.
Figure 19:
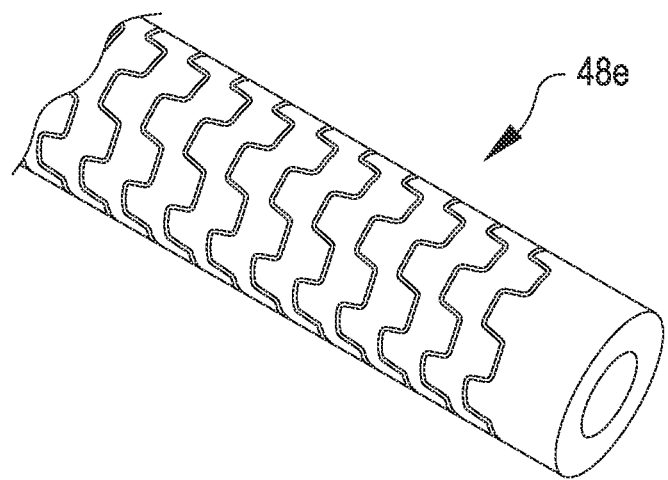
FIG. 19 shows another embodiment of a pushing assembly of an actuation assembly of the surgical tool of FIGS. 1-6.

The pushing assembly 48 is not limited to a close-coiled spring design illustrated in FIGS. 10-16. For example, FIG. 17-19 show flexible pushing assembly 48c, 48d, 48e that can be formed from a solid tube by locally cutting a pattern into the solid tube in the vicinity of the wrist 24 to increase bending flexibility of the pushing assembly at the wrist 24 without materially decreasing compressive stiffness. The pushing assembly 48c, 48d, 48e can be formed by laser cutting a pattern into a tube made from any suitable material (e.g., a suitable metal, a suitable polymer based material). In the pushing assembly 48c shown in FIG. 17, the pattern enhances flexibility where gaps are formed in the tube and retains axial stiffness where material is left in place. The pushing assembly 48d shown in FIG. 18 has a plurality of circumferential slits arranged in a spiraling pattern. In the pushing assembly 48e shown in FIG. 19, the pattern forms separate interlocking segments that provide flexibility while inhibiting relative dislocation of the interlocking segments.

Figure 20:
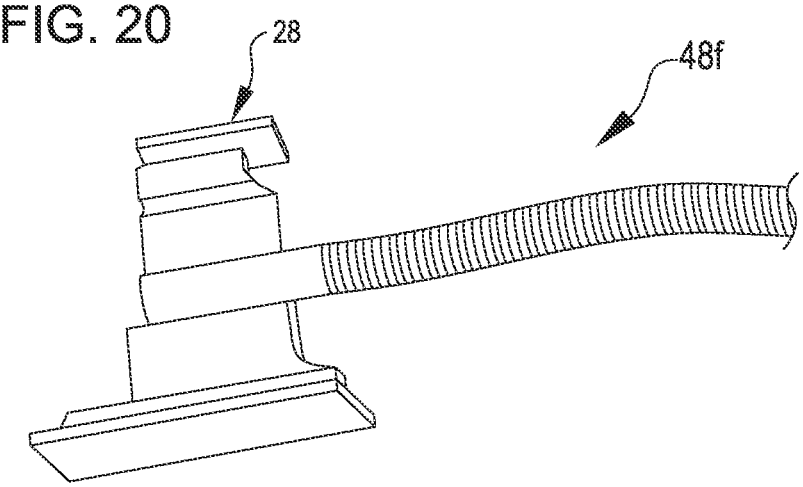
FIG. 20 shows a view of another embodiment of an actuation assembly of the surgical tool of FIGS. 1-6.
Figure 21:
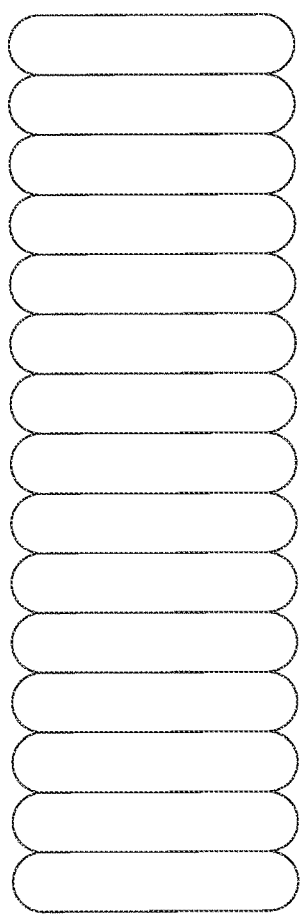
FIGS. 21 and 22 show another embodiment of a pushing assembly of an actuation assembly of the surgical tool of FIGS. 1-6.
Figure 22:
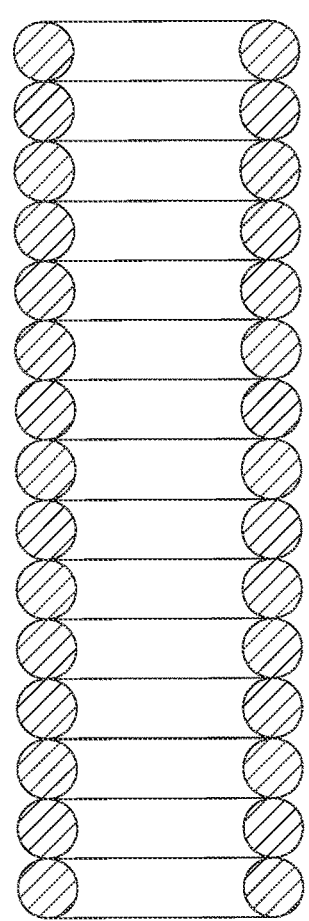
Figure 23:
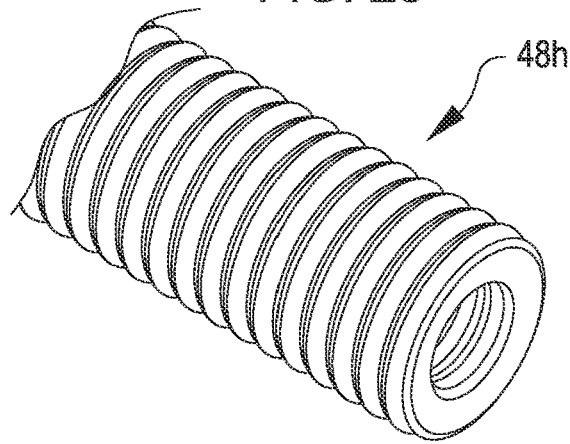
FIG. 23 shows another embodiment of a pushing assembly of an actuation assembly of the surgical tool of FIGS. 1-6.
Figure 24:
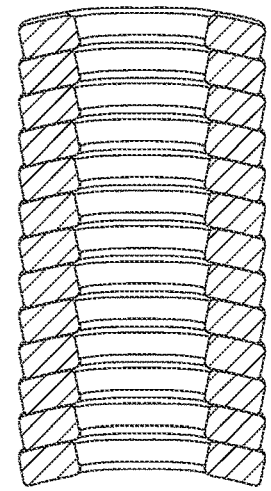
FIG. 24 shows a cross-sectional view of the pushing assembly of FIG. 23.

The pushing assembly 48 can be formed from any suitable configuration of separate interfacing segments. For example, FIG. 20 shows a pushing assembly 48f that is made from a stack of flat washers. FIG. 21 and FIG. 22 show a pushing assembly 48g that is made from a stack of torus disks. FIG. 23 and FIG. 24 show a pushing assembly 48h that is made from a stack of conical washers. Each of the conical washers has non-planar interfacing surfaces (e.g., spherical interfacing surfaces) that interact to inhibit relative transverse movement of the conical washers to enhance alignment of the conical washers with the pulling assembly 50, which extends through centers of the conical washers. As a result of the shape of the conical washers, the pushing assembly 48h accommodates bending of the pushing assembly 48h in any direction transverse to the local axial direction of the actuation assembly 46 via relative sliding in any direction between adjacent conical washers.

Figure 25:
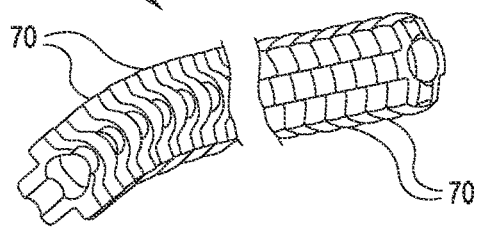
FIG. 25 shows another embodiment of a pushing assembly of an actuation assembly of the surgical tool of FIGS. 1-6.
Figure 26:
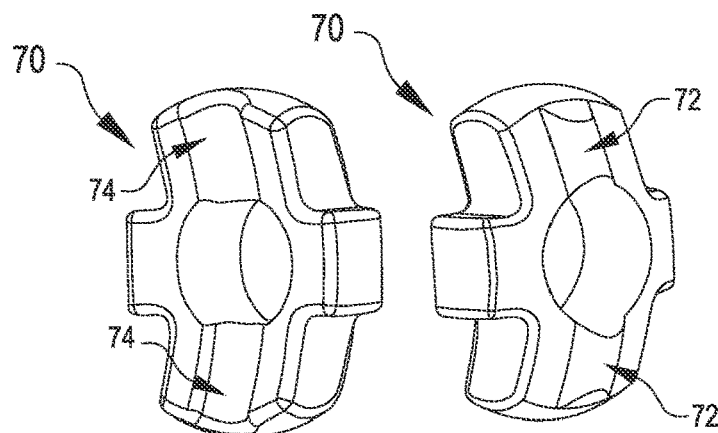
FIG. 26 shows views of an individual element of the pushing assembly of FIG. 25.

The pushing assembly 48 can be formed from a stack of any suitable non-axially-symmetric interfacing segments. For example, FIG. 25 shows a pushing assembly 48i that is made from a stack of separate non-axially-symmetric members 70. FIG. 26 shows different views of one of the members 70. In the embodiment shown, the member 70 has a transversely oriented protruding region 72 and a transversely oriented recessed region 74 shaped to accommodate and interface with the protruding region 72 of the adjacent member 70. The protruding region 72 and the recessed region 74 are shaped to limit relative sliding between adjacent members 70 to the direction in which the regions 72, 74 extend transverse to the local extending direction of the pushing assembly 48i. The interfacing regions 72, 74 also serve to inhibit relative twisting between adjacent members 70 around the local extending direction of the pushing assembly 48i, thereby inhibiting twisting of the pushing assembly 48i between the proximal and distal end of the pushing assembly 48i.

Figure 27:
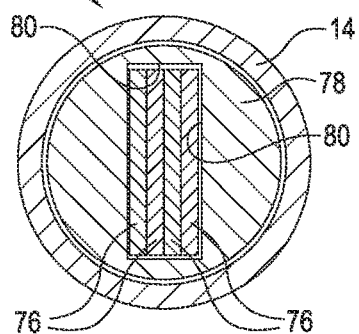
FIG. 27 shows a cross sectional view of another embodiment of an actuation assembly of the surgical tool of FIGS. 1-6.
Figure 28:
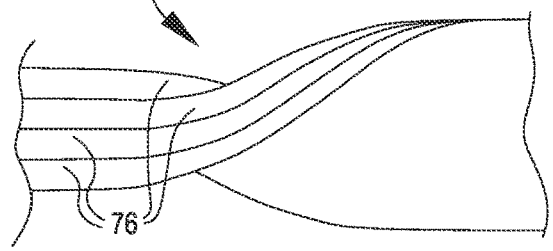
FIGS. 28 and 29 show top views of a portion of the actuation assembly of FIG. 27 located at a wrist of the surgical tool.
Figure 29:
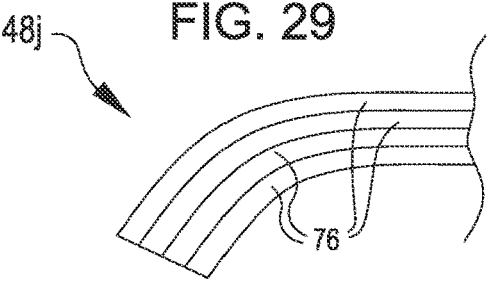

The actuation assembly 46 can include a stack of elongated sheet metal strips. For example, FIG. 27 shows a cross sectional view of an actuation assembly 46j of the surgical tool of FIGS. 1-6. The actuation assembly 46j includes elongated sheet metal strips 76 that are configured to react both compressive and tension loads while accommodating flexure of the actuation assembly 46j transverse to the plane of the sheet metal strips 76 as well as twisting of the actuation assembly 46j along the length of the actuation assembly 46j. The actuation assembly 46j includes an outer sheath 78 having a rectangular channel 80 through which the sheet metal strips 76 extend from the proximal end of the actuation assembly 46j to the distal end of the actuation assembly 46j. The outer sheath 78 constrains the stack of sheet metal strips 76 so as to prevent transverse buckling of the sheet metal strips 76 when the sheet metal strips are loaded in compression during distal advancement of the beam member 28. FIG. 28 illustrates twisting of the actuation assembly 46j and the associated twisting of the sheet metal strips 76 that may be induced in response to rotation of the end effector 16 relative to the instrument shaft 14. FIG. 29 illustrates flexure of the sheet metal strips 76 in the vicinity of the wrist assembly 24 that can be induced in response to reorientation of the end effector 16 relative to the instrument shaft 14.

The actuation assembly 46 can include a stack of elongated sheet metal bands to transmit tension load between the drive rod 52 and the beam member 28 and a stack of rectangular washers to transmit compression load between the drive rod 52 and the beam member 28. For example, FIG. 30 shows a isometric view of a actuation assembly 46k that includes a stack of sheet metal strips 76 that are attached to and extend between the drive rod 52 and the beam member 28. In the actuation assembly 46k, the sheet metal strips 76 transmit tension load from the drive rod 52 to the beam member 28 during proximal retraction of the beam member 28. The actuation assembly 46k further includes a stack of rectangular washers 82 that transmit compression load from the drive rod 52 to the beam member 28 during distal advancement of the beam member 28. The actuation assembly 46k further includes an inner sheath 84 having a lumen that accommodates the rectangular washers 82 and an outer sheath 86 having a lumen that accommodates the inner sheath 84. In the embodiment shown, the outer sheath 86 has a series of recesses 88 in the vicinity of the wrist assembly 24 to increase the flexibility of the outer sheath 86 to bend transverse to the plane of the sheet metal strips 76 in response to reorientation of the end effector 16 relative to the instrument shaft 14 via the wrist 24.

The actuation assembly 46 can include a plurality of flexible actuation rods. For example, FIG. 31 shows a side view of a distal portion of a actuation assembly 46m of the surgical tool of the surgical tool of FIGS. 1-6. The actuation assembly 46m includes three flexible actuation rods 90 that are adapted to transmit both tension force from the drive rod 52 to the beam member 28m and compression force from the drive rod 52 to the beam member 28m. The three flexible actuation rods 90 are aligned in a common plane thereby accommodating flexure of the actuation rods 90 transverse to the common plane. The three flexible actuation rods 90 are separately routed between the drive rod 52 and the beam member 28m, thereby accommodating twisting of the actuation rods 90 that may be induced in response to rotation of the end effector 16 relative to the instrument shaft 14. FIG. 32 shows an end view of the beam member 28m of the actuation assembly 46g that illustrates apertures 92 in the beam member 28m via which the actuation rods 90 are coupled to the beam member 28m.

The actuation assembly 46 can employ an element in place of the pulling assembly 50 that transmits both compression and tension loads from the drive rod 52 to the beam member 28. For example, FIG. 33 shows a actuation assembly 46n that includes a Nitinol wire 50a in place of the pulling assembly 50. The Nitinol wire 50a transmits both compressive and tensile loads from the drive rod 52 to the beam member 28 to both distally advance and proximally retract the beam member 28. In the illustrated embodiment, the actuation assembly 46n includes a spring 48n, which can be a closed coil spring but does not have to be. The spring 48n can be configured to share transmission of compressive load from the drive rod 52 to the beam member 28 with the Nitinol wire 50a during distal advancement of the beam member 28. The spring 48n can also be configured to not share transmission of compressive load from the drive rod 52 to the beam member 28 with the Nitinol wire 50a during distal advancement of the beam member 28. In many embodiments, the primary function of the spring 48n is to provide radially support to the Nitinol wire 50a so that the Nitinol wire can have a diameter consistent with the diameter of the drive rod 52. Any suitable approach can be used to attach the Nitinol wire 50a with each of the beam member 28 and the drive rod 52 such as, for example, swaging soldering, welding, etc.

Figure 34:
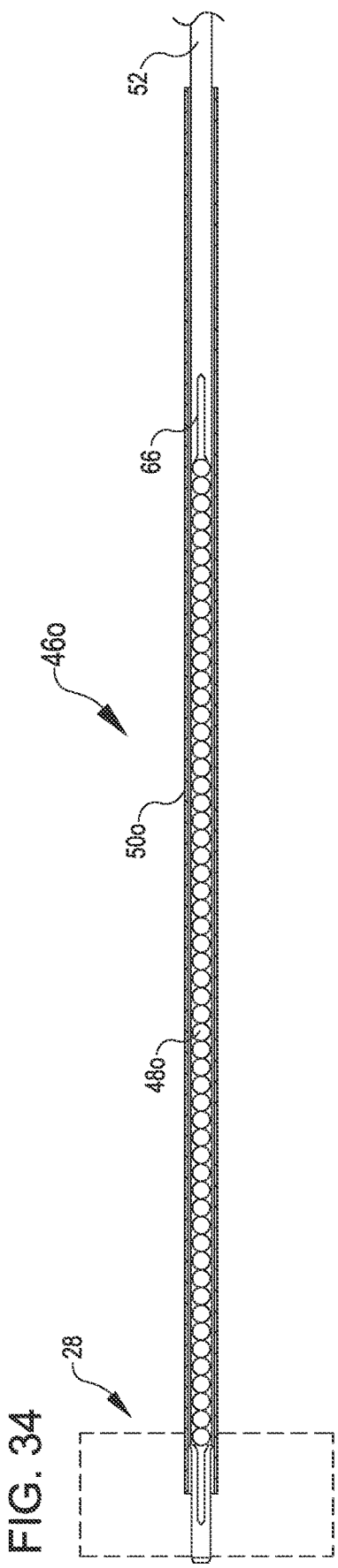
FIG. 34 shows a cross-sectional view of another embodiment of an actuation assembly of the surgical tool of FIGS. 1-6.

In some embodiments of the actuation assembly 46, the pushing member 48 is disposed within a lumen of the pulling member 50. For example, FIG. 34 shows an actuation assembly 46o including a pushing assembly 48o and a pulling assembly 50o having a lumen in which the pushing assembly 48o is disposed. The configuration of the actuation assembly 46o differs from other embodiments described herein in which the pushing assembly 48 concentrically surrounds the pulling assembly 50. In the actuation assembly 46o, the pulling assembly 50o comprises a sheath (e.g., a braided sheath) that encapsulates the pushing assembly 48o. The pushing assembly 48o includes a plurality of spherical members (e.g., ball bearings) joined by a flexible rod 66. Both the pushing assembly 48o and pulling assembly 50o are actuated by the drive rod 52, which is drivingly coupled to one or more of the input couplers 22 shown at FIG. 1.

Figure 35:
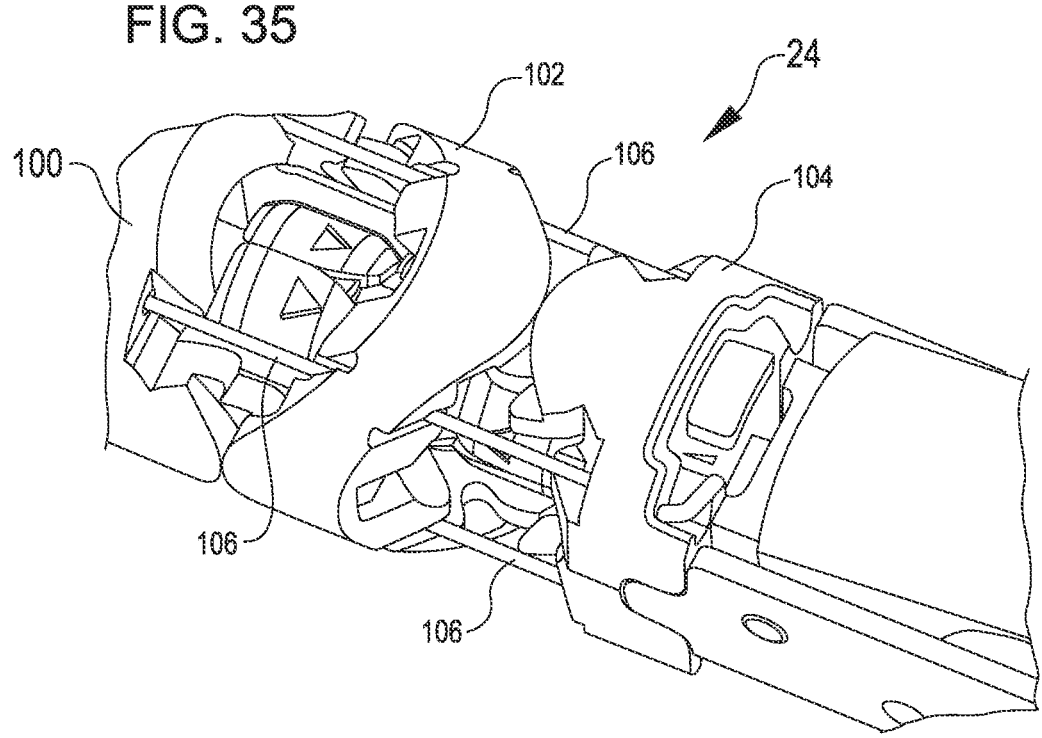
FIG. 35 shows a view of a wrist assembly of the surgical tool of FIGS. 1-6.
Figure 36:
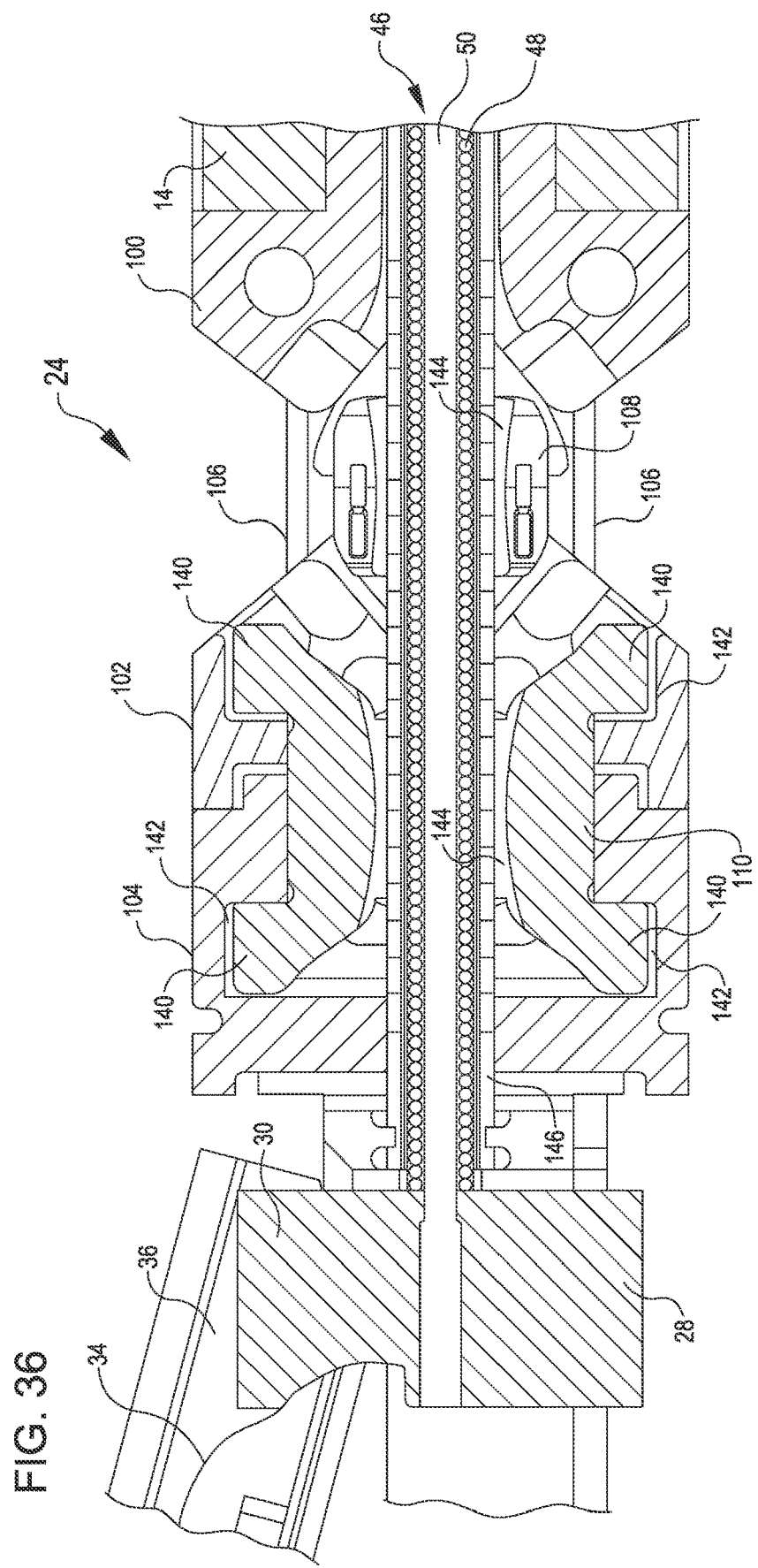
FIG. 36 shows a cross-sectional view of the wrist assembly of FIG. 35.

FIGS. 35 and 36 show perspective and cross-sectional views of the wrist assembly 24. The wrist assembly 24 includes a proximal outer link 100, a middle outer link 102, and a distal outer link 104. These three links determine the kinematic pitch and yaw motion of the wrist assembly 24. As shown, the interface between the proximal outer link 100 and the middle outer link 102 determine yaw movement of the wrist assembly 24. And the interface between the outer distal link 104 and the middle outer link 102 determine pitch movement of the wrist assembly 24. However, in an alternative wrist configuration, this relationship can be reversed such that the wrist assembly 24 pitches between the proximal outer link 100 and the middle outer link 102 and yaws between the distal outer link 100 and the middle outer link 102 (e.g., by rotating the end effector 16 relative to wrist assembly 24 by 90 degrees).

Cable portions 106 tension the wrist assembly 24 and actuate to impart motion to the wrist assembly. In one embodiment, cable portions 106 can be individually secured to a portion of the distal outer link 104. In an functionally equivalent alternate embodiment, as shown at FIG. 35, cable portions 106 are looped about a portion of the distal outer link 104. Looping cable portions 106 to the distal outer link 104 secures the cable portions 106 to the distal outer link 104 and prevents the cable portions 106 from slipping. In either embodiment, tension is applied to individual cable portions 106 to be pulled to articulate the wrist. Differential forces applied to the cable portions 106 can actuate the wrist assembly to pitch and yaw at various angles. The cable portions 106 can be drivingly coupled to one or more of the input couplers 22 shown at FIG. 1. The wrist assembly also includes proximal inner link 108 and distal inner link 110, which are discussed in detail below.

Figure 37:
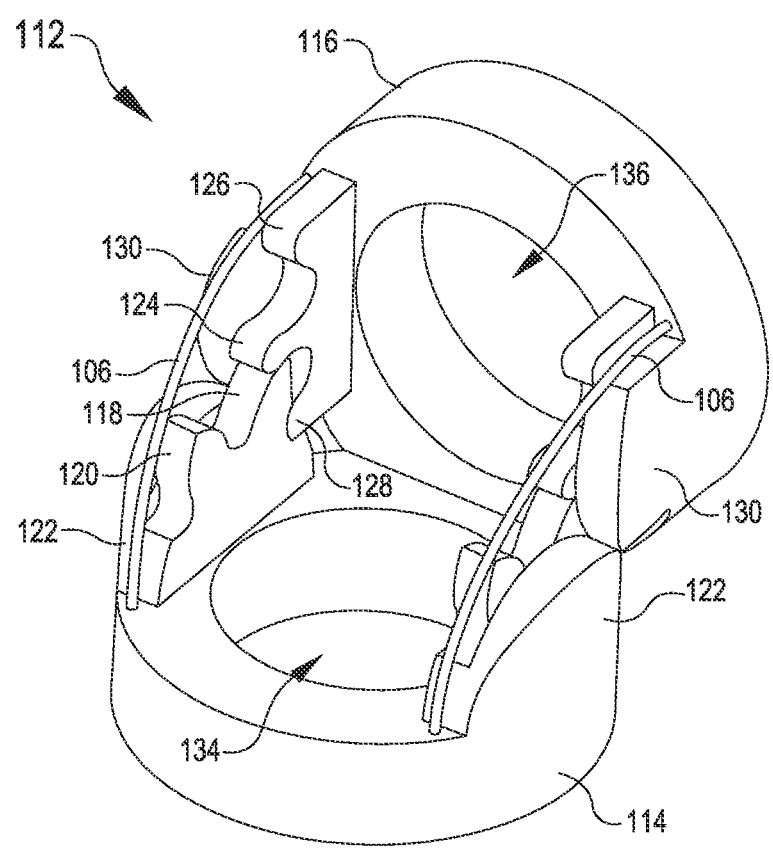
FIG. 37 shows a perspective view of an outer link assembly, according to some embodiments of the invention.

With attention to FIG. 37, an exemplary embodiment of a joint 112 is shown that is representative of the interfaces between the outer links shown at FIGS. 35 and 36. The joint 112 includes a first link 114 and a second link 116. First link 114 may include teeth 116, 118 and a bearing projection 122. Disc 720 may include pins 124, 126, 128 and a bearing projection 130. According to an exemplary embodiment, projections 122, 130 of first and second links 114, 116 may include passages to permit cable portions 106 to pass through. Because bearing projections 122, 130 are located at an outboard location relative to central apertures 134, 136 cable portions 106 extending through passages adjacent to bearing projections 122, 130 also are located at an outboard location. This allows for routing of other mechanisms through the central apertures 134, 136. Actuation kinematics between the links are determined by the shape of the pins and teeth, which engage and disengage during movement. The bearing projections 122, 130 included curved surfaces which engage at some point throughout all angular motion to help reduce compressive strain to the pins and teeth.

Due to the enhanced range of motion provided by joint 112, a wrist including joint 112 may provide a desired amount of motion, such as +/−90 degrees in a pitch or yaw direction, in a more efficient manner with fewer parts. In previous wrist structures in which each joint is limited to a maximum roll angle of about 45 degrees, several such joints in series are needed to relatively large roll angle for the entire wrist mechanism. And as illustrated, a single joint can provide up to a 90 degree roll angle limit. As a result, a manufacturing cost and complexity for a wrist that includes one or more joints 112 may be reduced while still achieving desired control over articulation. In addition, the plurality of teeth and corresponding plurality of pins included in links 114,116 of joint 112 can provide enhanced timing to assist with accurately positioning links 114,116, including, for example, returning discs to a neutral position (e.g., zero angle roll alignment), and to enhance smoothness of the motion between links 114,116, such as when links 114,116 are rotated in direction relative to one another. According to an exemplary embodiment, a wrist may include a plurality of joints 112 to achieve higher ranges of motion (up to roll limit angles), such as, for example, wrists having a range of motion of up to +/−180 degrees in a pitch or yaw direction. Additional details of joint 112, and other joints usable with the embodiments disclosed herein, are disclosed in Int'l. Pub. No. WO 2015/127250, which is incorporated by reference herein.

As shown at FIG. 36, the proximal and distal inner links 108,110 are spatially separated along axis 1 and offset 90 degrees from one another. Hence, the proximal internal link 108 is only partially shown. Radial surfaces of the proximal and distal inner links 108,110 include protrusions (e.g. configured as clevis pins 140). The clevis pins connect between indentations (e.g. configured as clevis joints 142) at medial surfaces of the external links. The clevis pins and joints 140, 142 set the distances between the joints of the outer links, but otherwise are passive and do not alter joint kinematics of the outer links, which is determined by the tooth and pin geometry. Each side of the proximal and distal inner links 108,110 includes a pair of commonly aligned clevis pins for each connection to an outer link for a total of four clevis pins per inner link 108,110. Each pair of clevis pins 140 is separated to provide an internal passage 144 for the actuation assembly 46.

An additional internal sheath 146 can be used to further support the actuation assembly 46. The actuation assembly 46 slides axially within the internal sheath 146. The internal sheath 146 is fixed to a distal end portion of the wrist assembly 24 and is flexible to bend with movement of the wrist assembly 24 but does not move axially. The internal sheath 146 and internal passage 144 provided by the inner links serve to guide and constrain the actuation assembly 46 during axial movement. Internal sheath 146 and inner passage 144 prevent the actuation assembly from buckling under compressive loading (i.e. distal movement while cutting and stapling). Prior wrist designs, such as disclosed in the aforementioned Int'l. Pub. No. WO 2015/127250, rely on tensioned cables to maintain the outer links in position. Here, that would be unsatisfactory because when the actuation assembly 46 moves in a distal direction the resulting compressive force may induce slack in the cables. The clevis pins 140 of the inner links 108,110, however, advantageously maintain the outer links in position when the actuation assembly 46 moves in a distal direction, therefore maintaining the structure of the wrist assembly 24.

Figure 38:
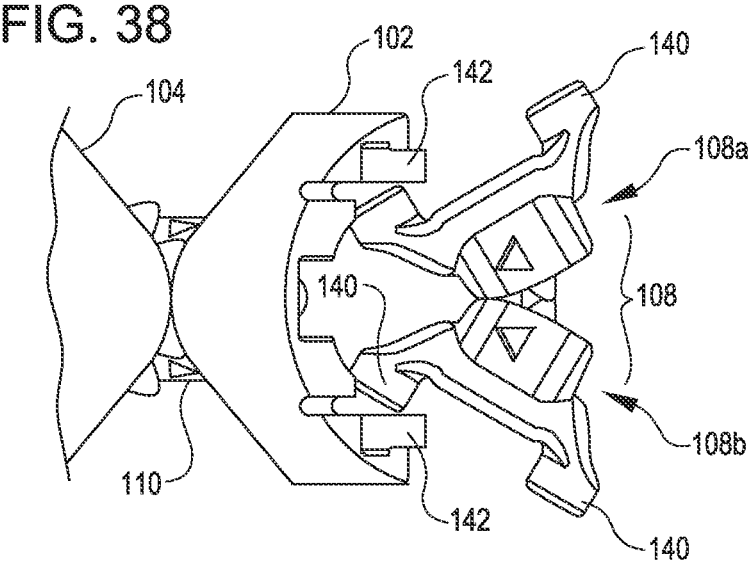
FIGS. 38-40 show a method of assembling a wrist assembly, according to some embodiments of the invention.
Figure 39:
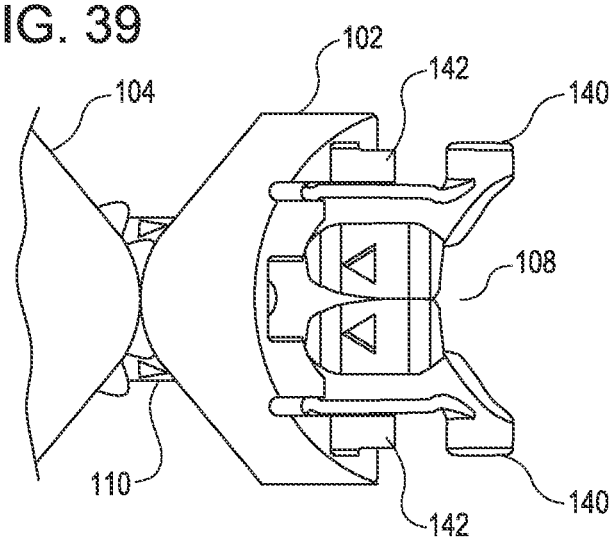
Figure 40:
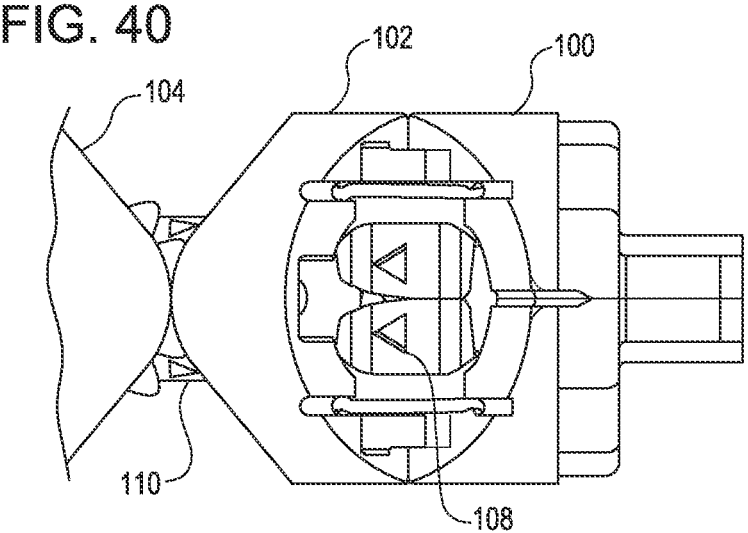

Each inner link can have a two-piece construction as depicted at FIGS. 38 through 40, which also depict a technique for assembling the inner links to the outer links. At FIG. 38 first link portion 108a and second link portion 108b of the proximal inner link 108 are positioned to place clevis pins 140 into clevis joints 142 of the middle outer link 102. The first link portion 108a and second link portion 108b are inserted at angles such that gear teeth 148 of each portion intermesh to cause alignment of the portions into the formation shown at FIG. 39. The gear teeth 148 are an assembly aid that eliminates the need for pins or other fasteners, and are not used for movement beyond assembly. However, in some embodiments, fasteners can be used in lieu of the gear teeth. After the link portions 108a, 108b are assembled into a complete inner proximal link 108, the proximal outer link 100 is assembled onto the remaining exposed clevis pins 140 into the formation shown at FIG. 40. In one embodiment, as shown at FIG. 40, proximal outer link 100 is also of two-piece construction.

Other variations are within the spirit of the present invention. The various aspects, embodiments, implementations or features of the described embodiments can be used separately or in any combination. Various aspects of the described embodiments associated with operation of telesurgical tools can be implemented by software, hardware or a combination of hardware and software. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A surgical tool comprising:
   an end effector;
   an instrument shaft;
   a wrist assembly moveably connecting the end effector to the instrument shaft, wherein the wrist assembly is operable to articulate the end effector relative to the instrument shaft about two orthogonal axes relative to the instrument shaft, wherein the wrist assembly comprises a proximal outer link, a proximal inner link having a pair of intermeshing portions, a middle outer link, a distal inner link having a pair of intermeshing portions, and a distal outer link, wherein the middle outer link is pivotally coupled with the proximal outer link by the intermeshed pair of proximal inner link portions for articulation of the middle outer link relative to the proximal outer link around a first of the two orthogonal axes, wherein the distal outer link is pivotally coupled with the middle outer link by the intermeshed pair of distal inner link portions for articulation of the distal outer link relative to the middle outer link around a second of the two orthogonal axes, wherein the proximal inner link comprises a proximal inner link inner passage, and wherein the distal inner link comprises a distal inner link inner passage;

cable portions secured to the distal outer link and articulatable to articulate the wrist assembly; and an actuation assembly comprising a pushing assembly that transfers compressive force to the end effector and a pulling assembly that transfers tensile force to the end effector, wherein the actuation assembly extends through the proximal inner link inner passage and the distal inner link inner passage.

2. The surgical tool of claim 1, wherein:

the instrument shaft extends along a first axis;

the proximal inner link is pivotally coupled with the proximal outer link to rotate relative to the proximal outer link around a second axis oriented perpendicular to the first axis;

the middle outer link is pivotally coupled with the proximal inner link to rotate relative to the proximal inner link around a third axis parallel to the second axis and offset from the second axis;

the distal inner link is pivotally coupled with the middle outer link to rotate relative to the middle outer link around a fourth axis; and the distal outer link is pivotally coupled with the distal inner link to rotate relative to the distal inner link around a fifth axis parallel to the fourth axis and offset from the fourth axis.

3. The surgical tool of claim 1, further comprising:

a proximal chassis configured to be detachably mounted to a robotic manipulator, wherein the proximal chassis comprises an input coupler configured to be interfaced with and driven by an output coupler of the robotic manipulator; and a drive rod located in the instrument shaft and drivingly coupled with the input coupler for translation of the drive rod relative to the instrument shaft, wherein the actuation assembly is attached to a distal end of the drive rod.

4. The surgical tool of claim 1, wherein the pulling assembly comprises an elongated cable.

5. The surgical tool of claim 4, wherein the pushing assembly comprises an inner lumen surrounding the elongated cable.

6. The surgical tool of claim 5, wherein the pushing assembly comprises a close-coiled spring.

7. The surgical tool of claim 6, wherein the close-coiled spring has a cylindrical outer surface.

8. The surgical tool of claim 6, wherein the close-coiled spring has interfacing convex and concave surfaces.

9. The surgical tool of claim 6, wherein close-coiled spring comprises a spiral cut tube.

10. The surgical tool of claim 5, wherein the pushing assembly comprises a tube having a pattern of recesses.

11. The surgical tool of claim 1, wherein the pushing assembly comprises pushing elements that separate under tension.

12. The surgical tool of claim 1, wherein the pushing assembly comprises separate elements having interfacing surfaces that limit transverse relative sliding between the separate elements to one direction.

13. The surgical tool of claim 1, wherein the pushing assembly comprises separate elements having interfacing surfaces that inhibit relative twisting between the separate elements.

14. The surgical tool of claim 1, wherein the pushing assembly comprises a stack of flat washers.

15. The surgical tool of claim 1, wherein the pushing assembly comprises a stack of torus disks.

16. The surgical tool of claim 1, wherein the pulling assembly comprises sheet metal bands.

17. The surgical tool of claim 16, wherein the pushing assembly comprises a stack of rectangular washers defining a lumen through which the sheet metal bands extends.

18. The surgical tool of claim 1, wherein the intermeshing portions include gear teeth.

* * * * *